United States Patent [19]
Gawel et al.

[11] Patent Number: 4,999,286
[45] Date of Patent: Mar. 12, 1991

[54] SULFATE REDUCING BACTERIA DETERMINATION AND CONTROL

[75] Inventors: Len J. Gawel, Ponca City, Okla.; Thomas Ng, Portola Valley, Calif.; James M. Odom; Richard C. Ebersole, both of Wilmington, Del.

[73] Assignee: E. I. du Pont de Nemours and Company, Wilmington, Del.

[21] Appl. No.: 946,547

[22] Filed: Dec. 23, 1986

[51] Int. Cl.$^5$ .................... G01N 33/50; G01N 33/53; C12Q 1/68
[52] U.S. Cl. .................... 435/7.32; 435/4; 435/9; 435/25; 435/29; 435/34; 435/7.4; 435/7.8; 436/518; 436/531
[58] Field of Search .................... 435/4, 7, 9, 25, 29, 435/34, 807, 809, 81 D, 920; 436/518, 547, 47, 52, 63, 175, 177, 501; 514/515, 516, 517

[56] References Cited

U.S. PATENT DOCUMENTS

| | | | |
|---|---|---|---|
| 3,198,733 | 8/1965 | Pera et al. | 252/8.55 |
| 3,300,375 | 1/1967 | Wehner | 514/516 |
| 3,551,295 | 12/1970 | Dyer | 435/34 |
| 4,098,876 | 7/1978 | Pissio et al. | 424/1 |
| 4,166,765 | 9/1979 | Weetall | 435/26 |
| 4,188,371 | 2/1980 | Weetall | 424/1 |
| 4,245,038 | 1/1981 | Weetall | 435/7 |

FOREIGN PATENT DOCUMENTS 0198413 10/1986 European Pat. Off. .

OTHER PUBLICATIONS

Fenn et al., Clinics in Laboratory Medicine, vol. 5, No. 1, Mar. 1985, pp. 19-21.
Biotechnology News, Aug. 15, 1986.
Arch. Microbiol. 133 118-121 (1982) By A. D. Smith.
Applied and Environmental Microbiology 50: 31-37 1985, Norquist et al.
International Symposium on Gonorrhea, B. B. Diena Ed., Oct. 1973, pp. 34-43.
Widdel-Anaerobic Bacteria in Habitats Other Than Man, 1986, eds. Barnes-Mead.
Microbial Chemautotrophy, H. D. Peck, ch. 18, pp. 309-335.
Singleton et al., Arch. Microbiol. 139: 91-94 (1984).
Skyring et al., Can. J. Microbiol., 19: 375-380 (1973).
Stille et al., Arch. Microbiol. 137: 140-150 (1984).
Aketagawa et al., J. Gen. Appl. Microbiol. 31: 347-357 (1985).

Primary Examiner—Esther M. Kepplinger
Assistant Examiner—Carol A. Spiegel

[57] ABSTRACT

Sulfate reducing bacteria are detected by preparing a lysate so as to release an enzyme essential to derive energy by reduction of sulfate such as adenosine 5'-phosphosulfate reductase (APS reductase), containing the lysate with an antibody for the enzyme, and detecting the presence of the reaction product of the enzyme and the antibody. In one aspect, sulfate reducing bacteria are controlled responsive to such assay. In another aspect, a "test kit" is provided for carrying out the assay.

8 Claims, 6 Drawing Sheets

SULFATE REDUCING BACTERIA DETERMINATION AND CONTROL

BACKGROUND OF THE INVENTION

1. Field of the Invention

The invention relates to improved control of deleterious sulfate-reducing bacteria which produce corrosion and noxious sulfide ions or sourness in aqueous environments, particularly oil reservoirs, oil and gas wells, pipelines, vessels, cooling towers, and the like.

In one aspect, the invention relates to a process for determining the presence of sulfate-reducing bacteria in an aqueous environment utilizing an immunoassay technique.

In another aspect, the invention relates to apparatus for determining the presence of sulfate-reducing bacteria.

2. Brief Description of the Prior Art

Sulfate-reducing bacteria are strictly anaerobic eubacteria. They have considerable physiological and morphological diversity, and no simple classification scheme is recognized. They are variously classified in at least the following genera: Desulfovibrio, Desulfotomaculum, Desulfomonas, Desulfobacter, Desulfobulbus, Desulfococcus, Desulfonema, Desulfosarcina, and Thermodesulfobacterium. Furthermore, morphological or physiological similarities among the sulfate-reducing bacteria do not necessarily reflect close generic relationships. The sulfate-reducing bacteria only have in common their ability to utilize sulfate as a terminal electron donor and the fact that they are all anaerobes. When the term "sulfate-reducing bacteria" is used herein these two criteria apply, regardless of taxonomic classification, even to the extent that microbes other than "bacteria" might be included.

In nature, the sulfate-reducing bacteria exploit an ecological niche wherein anaerobic conditions prevail. The greatest variety of sulfate-reducing bacteria is found in nature in permanently anaerobic sulfate rich sediments of low or moderate temperature and salinities, such as the reduced zone in sediments of estuaries and marine habitats. Reduction of the sulfate ion, ultimately to $H_2S$, is employed in lieu of reduction of oxygen. Nearly all compounds known to be degradation products of carbohydrates, proteins, nucleic acids, and lipids are utilized by the sulfate-reducing bacteria. Typical electron donors for sulfate-reducing bacteria are $H_2$, formate, acetate, propionate, higher straight and branched chain fatty acids, monohydroxy alcohols, lactate, dicarboxylic acids, phenyl-substituted carboxylic acids, and related cyclic compounds. In short, they like an anaerobic aqueous medium having sulfate ions to "breathe" and metabolic leftovers to "eat".

Therein lies the problem.

Many industries, including the oil and gas industry, the chemical industry, the electric utility industry, and several other industries have created almost ideal habitats for the sulfate-reducing bacteria in their operations. For example, sulfate-reducing bacteria can infest an oil reservoir, particularly when a water flood is being conducted, so as to form large quantities of $H_2S$ and turn the reservoir sour with resulting corrosion, separation, and safety problems. Sulfate-reducing bacteria can inhabit well bores, pipelines and other tubulars, storage vessels, and the like causing production of $H_2S$ and severe corrosion problems. They may inhabit a biological niche below colonies of other microorganisms in vessels, pipelines, on cooling towers, and elsewhere, and thus form $H_2S$ and/or other metabolic products that also cause severe corrosion problems.

Though a variety of control measures can be employed to halt or mitigate the deleterious effects of the sulfate-reducing bacteria in such industrial operations, typically, particularly in the oil industry, a bactericidal or bacteriostatic agent is introduced into the system. For example, chlorine, ozone, acrolein, quaternary ammonium salts, peroxides, or a number of other known measures can be employed.

However, in order for control measures to be both effective in controlling sulfate-reducing bacteria infestations, while yet being cost effective and not introducing unnecessary deleterious effects into the system, better methods are needed to determine the presence and/or quantity of sulfate-reducing bacteria present in the environments to be treated.

Consequently, efforts have been made to develop a method for determining sulfate-reducing bacteria in aqueous environments. It is desirable that a means to detect these bacteria be capable of use in the field, be broad yet reliable, sensitive, quantitative, rapid, and simple enough that it can be performed by untrained personnel. An immunological means of detecting essentially all of the sulfate-reducing bacteria, meeting the above criteria is a subject of this invention. It is possible because the genera of sulfate-reducing bacteria contain unique enzyme proteins which nevertheless share an antigenic site.

A detailed discussion of selected relevant prior art references follows:

In Biotechnology News, Aug. 15, 1986, a kit based on a half dozen polyclonal antibody preparations to the surface antigens of different sulfate-reducing bacteria and immunofluorescence assays for the purpose of detecting sulfate-reducing bacteria was disclosed. There are two mixtures of the antibodies, one for marine applications and one for use on land. The kit described above, based on antibodies to surface antigens known to be different among the different genera of sulfate-reducing bacteria, requires mixtures of antibodies and must rely on the assumption that a mixture contains an antibody to every genus and species of sulfate-reducing bacteria likely to be encountered.

A paper by A. D. Smith, Arch. Microbiol. 133: 118-121 (1982), illustrates the possible weakness of the use of surface antigens for the identification of sulfate-reducing bacteria. Five specific antisera were prepared against 5 strains of sulfate-reducing bacteria and one polyvalent antiserum was prepared by mixing equal volumes of the five specific antisera. The sera were tested against 44 strains of the genera Desulfovibrio and Desulfotomaculum along with 4 control organisms. Immunological reactivity was mainly strain specific although weak reactivity was seen both within and between groups. None of the antisera including the polyvalent antiserum successfully detected all the sulfate-reducing bacteria in the test. Cross reactivity with control bacteria was weak or absent.

Norqvist et al., Applied and Environmental Microbiology 50: 31-37 (1985), disclose that the envelope proteins of some strains of Desulfovibrio were quite different and that the envelope proteins of at least one species of Desulfotomaculum was unique from that of several other species. This study illustrates why one would not expect antisera against surface antigens to cross react adequately to detect sulfate-reducing bacteria of different genera. It also points out the diversity of protein envelope molecules among the sulfate-reducing bacteria.

Use of antibodies against surface antigens to detect bacteria has been previously used in detecting other bacteria. For example, a need to be able to quickly and accurately detect the presence of the genus Neisseria (the organism causing gonorrhea) exists. One of the conventional tests uses serological methods. Limitations of the use of serological methods for these bacteria were pointed out in the publication "International Symposium on Gonorrhea", B. B. Diena, Ed., a collection of papers presented at the October, 1973 International Symposium on Gonorrhea sponsored by the Health Protection Branch, Health and Welfare Canada, Ottawa, in the chapter entitled "Uses and Limitations of Serologic Tests for Gonorrhea: An Overview" by L. C. Norins, P 34–43.

To overcome the limitations of detection of Neisseria by antibodies to bacterial surface antigens, H. H. Weetall, U.S. Pat. No. 4,166,765, U.S. Pat. No. 4,188,371 and U.S. Pat. No. 4,245,038, developed several relatively simple and quick tests for the presence of Neisseria in liquid samples founded upon the discovery of an enzyme in Neisseria bacteria which is specific to the genus Neisseria. An antiserum was prepared against the enzyme tentatively identified as 1,2-propanediol dehydrogenase from Neisseria bacteria and used in an immunoassay to detect the presence of said enzyme in lysates of bacterial samples.

In the present application, it is disclosed that antibodies to a purified preparation of the enzyme adenosine 5'-phosphosulfate reductase (APS reductase) from one genus of sulfate-reducing bacteria surprisingly cross-reacts with molecules in lysates of the bacteria of other genera of sulfate-reducing bacteria.

As described by Widdel, in Anaerobic Bacteria in Habitats Other Than Man, 1986, eds. E. M. Barnes, and G. C. Mead, Blackwell Scientific, the sulfate-reducing bacteria consist of 8 genera. They are diverse both physiologically and morphologically, and the guanine plus cytosine content (a measure of closeness of composition of their DNA's) ranges widely, (from 34 to 67 mol %).

H. D. Peck, Chapter 18, pages 309–335, in Microbial Chemoautotrophy, edited by W. R. Strohl and O. H. Tuovinen, published by the Ohio State University Press, Columbus, Ohio discloses the physiological diversity of the sulfate-reducing bacteria.

Singleton, et al., Arch. Microbiol. 139: 91–94, (1984), using an indirect enzyme-linked immunosorption assay for cytochrome $c_3$ to study the immunological relatedness of cytochromes $c_3$ of different sulfate-reducing bacteria showed that cytochromes $c_3$ from various strains of the genus Desulfovibrio contain markedly different antigenic determinants. The authors concluded that the diversity of the sulfate-reducing bacteria may be much greater than has been previously supposed.

Skyring et al., Can. J. Microbiol., 19: 375–380 (1973), point out that the dissimilatory sulfate-reducing bacteria are so called because of their unique energy metabolism which is linked to the reduction of sulfate to hydrogen sulfide. They suggest that all of the sulfate-reducing bacteria may reduce sulfate by means of a common mechanism. They state that common biochemical ancestry may be reflected in similarities of enzymes of the sulfate reduction pathway more than of other cellular constituents. They compared the electrophoretic properties of three enzymes of the sulfate reduction pathway including adenosine 5'-phosphosulphate reductase (APS reductase) from 13 strains of dissimilatory sulfate-reducing bacteria from 2 genera. They found a similarity in the electrophoretic behavior of the APS reductase from some of the strains.

Stille et al. Arch. Microbiol. 137: 140–150 (1984) disclose a comparison of properties of APS reductases purified at the time of the study. The enzymes differ as they range in molecular weight from $1.7 \times 10^5$ to $2.2 \times 10^5$ and contain from 4 to 8 non heme iron atoms per molecule of enzyme. Other similarities and differences are disclosed.

Aketagawa et al. J. Gen. Appl. Microbiol. 31: 347–357 (1985) determined the immunological cross-reactivities among sulfite reductase, hydrogenases, and somatic antigens of 10 strains in 5 species of the single genus Desulfovibrio. They disclose that the sulfite reductases from Desulfovibrio share common antigenic determinants. However, the hydrogenases, which had different physico-chemical properties from strain to strain showed limited immunological cross-reactivities. The immunological cross-reactivities along with other known features of the sulfite reductases of Desulfovibrio suggest that the structure of the sulfite reductase has been conserved better than other cellular components during evolution. There was little immunological cross-reactivity among the hydrogenases from the 10 strains and in agreement with the previously cited results, none of the antisera against somatic antigens tested reacted with all the 10 species within the genus though there was cross-reactivity among some of the strains.

Despite all the heterogeneity of antigens and intracellular molecules of the sulfate-reducing bacteria as disclosed above, the present invention makes use of the findings that APS reductases in the sulfate-reducing bacteria share sufficient immunological cross-reacting sites to permit their detection by immunological means and thereby to serve as a means of detecting the presence of sulfate-reducing bacteria in lysed samples. Even though APS reductases are known to exist in some sulfide oxidizing bacteria, they do not have sufficient immunological cross-reactivity with those from sulfate-reducing bacteria to interfere with the detection of sulfate-reducing bacteria by the means of this invention.

Accordingly, the invention provides an improved method for controlling sulfate reducing bacteria in industrial operations, particularly in the oil industry. It provides apparatus for rapidly determining the presence and/or quantity of sulfate-reducing bacteria in an aqueous environment. It provides an accurate, easily conducted, and rapid method of detecting and/or quantifying sulfate-reducing bacteria in industrial systems, or elsewhere.

OBJECTS OF THE INVENTION

An object of the invention is to provide an improved method for controlling sulfate-reducing bacteria in aqueous environments. The presence, and if present, preferably the quantity of sulfate-reducing bacteria are determined by a very specific immunoassay, and a non-deleterious but effective amount of a bactericidal or bacteriostatic agent is introduced into the aqueous environment to control sulfate-reducing bacteria which are detected.

Another object of the invention is to provide a method for specifically detecting sulfate-reducing bacteria in an aqueous environment by an immunoassay method which is specific for an enzyme which the bacteria utilize to derive energy by reduction of sulfate, presently, preferably, adenosine 5'-phosphosulfate reductase.

Yet another object of the invention is to provide apparatus for rapid detection of sulfate-reducing bacteria in an aqueous environment by immunoassay utilizing an enzyme which the sulfate-reducing bacteria utilize to derive energy by reduction of sulfate, e.g., adenosine 5'-phosphosulfate reductase.

Other objects will be apparent to those skilled in the art upon reading the specification and claims of this application.

SUMMARY OF THE INVENTION

Sulfate-reducing bacteria in an aqueous environment are detected by: (a) preparing a lysate of a sample taken from the environment and selected so as to include any microbes present in the environment such as to release into the lysate an enzyme which the sulfate-reducing bacteria utilize to derive energy by reduction of sulfate moiety, (b) contacting at least a portion of the lysate with an antibody for the enzyme under reactive conditions for an antibody-enzyme reaction, and (c) detecting any presence of the reaction product of the enzyme and the antibody so as to determine the presence of sulfate-reducing bacteria. According to a presently preferred mode, the enzyme which is lysed from the sample and which is used to prepare the antibody is an adenosine 5'-phosphosulfate reductase which is situated inside the sulfate-reducing bacterial cell walls.

According to one aspect of the invention, an effective amount of a bactericidal or bacteriostatic agent for controlling sulfate-reducing bacteria is introduced into the aqueous environment when the sulfate-reducing bacteria are detected, and presently preferably in effective but not excessive or deleterious amounts.

According to yet another aspect of the invention, apparatus, presently preferably in the form of a "test kit" is provided for effecting the process or method of the invention. In one embodiment, the "test kit" can comprise a container having an access port and a capture reagent disposed in the container characterized in that the capture reagent comprises an antibody for APS reductase derived by injecting APS reductase from sulfate-reducing bacteria which has been purified of other proteins into an organism having an immune system, and then recovering the antibody for the APS reductase from the organism. In a presently preferred embodiment, the antibody for the APS reductase is bound or linked onto a solid phase support disposed in the container and capable of binding the antibody.

Reference is made to EPA Application No. 0198413 published in Europe on Oct. 22, 1986, and relating to U.S. Pat. No. 4,753,775 issued June 28, 1988. The EPA application is herewith referred to and incorporated by reference. Apparatus useful in carrying out the invention constitutes an improvement on the apparatus of that application.

BRIEF DESCRIPTION OF THE DRAWINGS

Apparatus constituting one aspect of the invention, relating to a "test kit" for effecting the process or method of the invention may be more fully understood from the following Detailed Description thereof taken in connection with accompanying drawings which form a part of EPA Application No. 0198413.

Figure 1A:
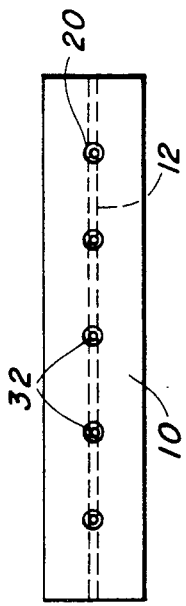
FIG. 1 is a partial block, partial schematic diagram of a multiport processor constructed in accordance with one form of this invention.

DETAILED DESCRIPTION OF APPARATUS OF THE INVENTION AS CONSTITUTING IMPROVEMENT IN APPARATUS SHOWN IN THE DRAWINGS

A presently preferred embodiment of the invention, as related to apparatus and systems for carrying out a preferred mode, may be seen and described with reference to drawings from EPA Application No. 0198413. Thus, the system may be seen to include a multiport manifold 10 defining a closed chamber in the form of a conduit 12 extending through the manifold. One end of the conduit 12 is connected through a valve 14 and a waste trap 16 to a source of vacuum 18. Typically this source would be a vacuum aspirator or pump. A plurality of receptacle ports 20 are formed in the upper portion of the manifold 10, each being adapted to receive a suitable receptacle or other rapid assay device, as will be described. Each port is configured to provide a vacuum tight seal which affords facile insertion and removal of the receptacle. The conduit 12 is also connected through a valve 17 to a source of gas 19; typically this is air at atmospheric pressure. The other end of the conduit 12 is connected through suitable valves 22 to respective sources of auxiliary reagent 24, wash fluid 26 and a substrate 28. Each of the valves 14, 19 and 22 in turn is controlled by a suitable process control unit 30.

Figure 8:
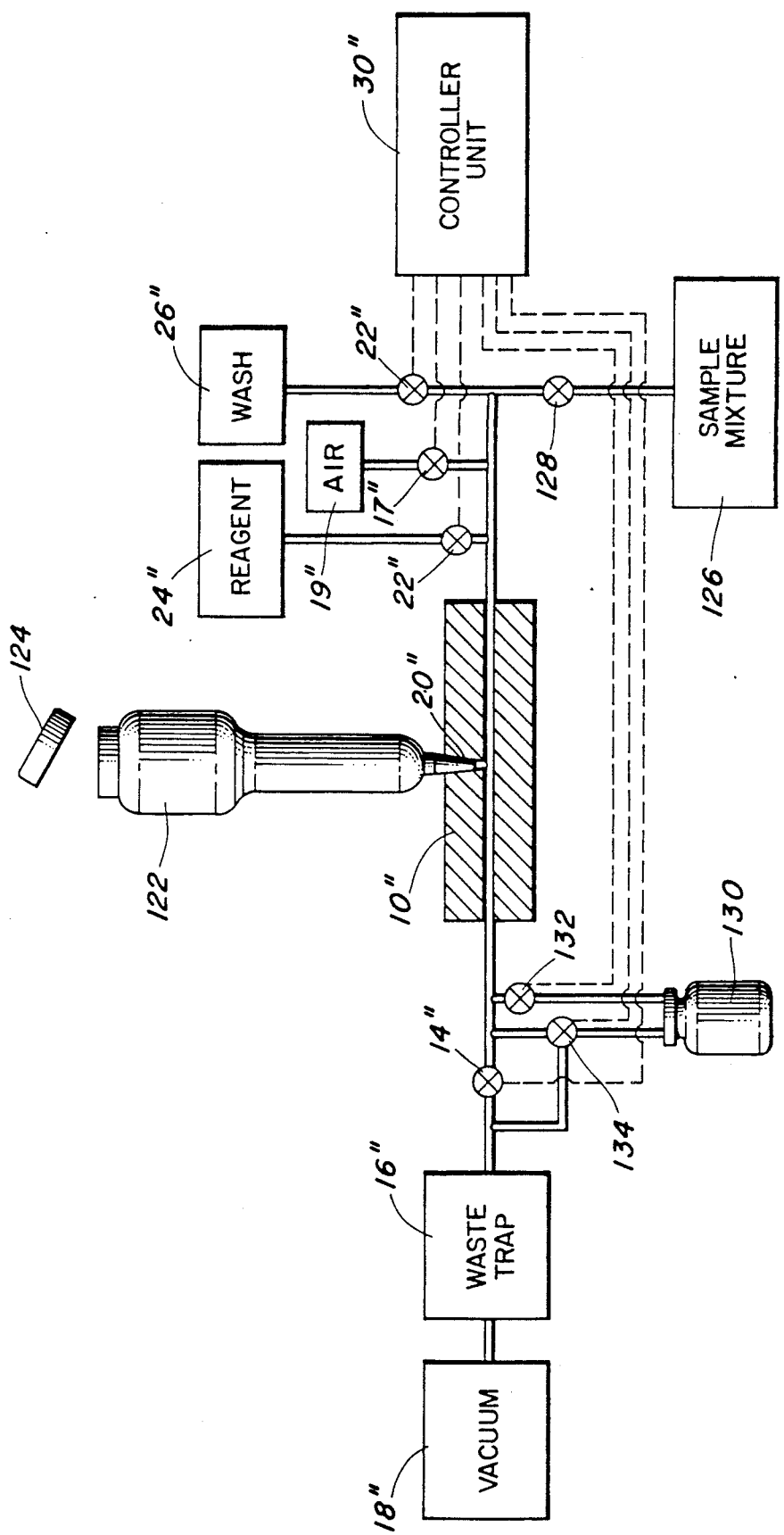
FIG. 8 is a partial block, partial schematic diagram of a multiport processor for isolating components of a complex mixture constructed in accordance with another embodiment of this invention.
Figure 9:
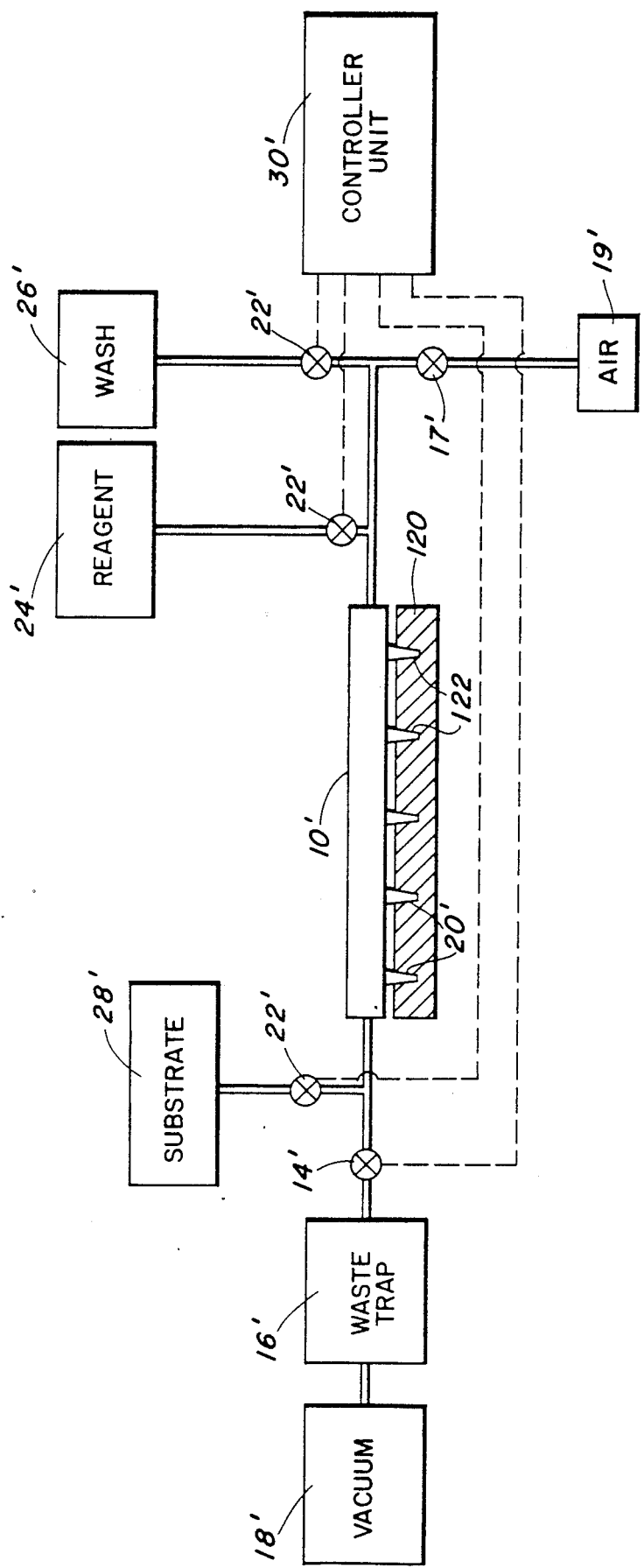
FIG. 9 is a partial pictorial, partial schematic diagram of the system of this invention modified to find use with a microtiter plate.

The seal for the ports 20 may be accomplished by configuring the ports to either have an interior taper, as shown, adapted to receive a similarly tapered receptacle tip 42 (FIG. 2) or if an exterior seal is desired, the manifold is provided with tapered stubs (not shown) adapted to fit inside a similarly tapered receptacle tip as will be described in conjunction with FIG. 8. In any event the ports 20 may be designed to accommodate a wide variety of different test devices and configurations.

The valves are preferably electronically controlled to control the access of the various fluids and sources of vacuum and air to the conduit 12. It is important in selecting the valve that they provide rapid on-off control within about 0.1 second. One suitable valve that has been found satisfactory is a pinch valve purchased from ACRO Air Associates of Concord, Calif. (Part #940121418). These valves used in combination with silicone rubber tubes for the interconnecting conduits were employed successfully in tests. Any suitable computer may be used for the controller unit 30. It need not be described further since computers of this type are well known. For example, an HP-85 computer has been successfully used for this purpose. The software for such computer will be described below. The vacuum source 18 should be a source capable of providing equal to or greater than 25 inches of mercury vacuum. One vacuum pump which has been used successfully is available from SGA Scientific in Bloomfield, N.J. Part #LV-6610.

Each of the ports 20 may be in the form of a tapered recess 32 formed in the top of the manifold 10 and communicating with the conduit 12. The manifold 10 may be formed of any suitable material that is chemically and biologically inert. Suitable materials for this purpose are polyethylene, polypropylene, or an ionomer resin such as "Surlyn" sold by E. I. du Pont de Nemours and Company.

Figure 1:
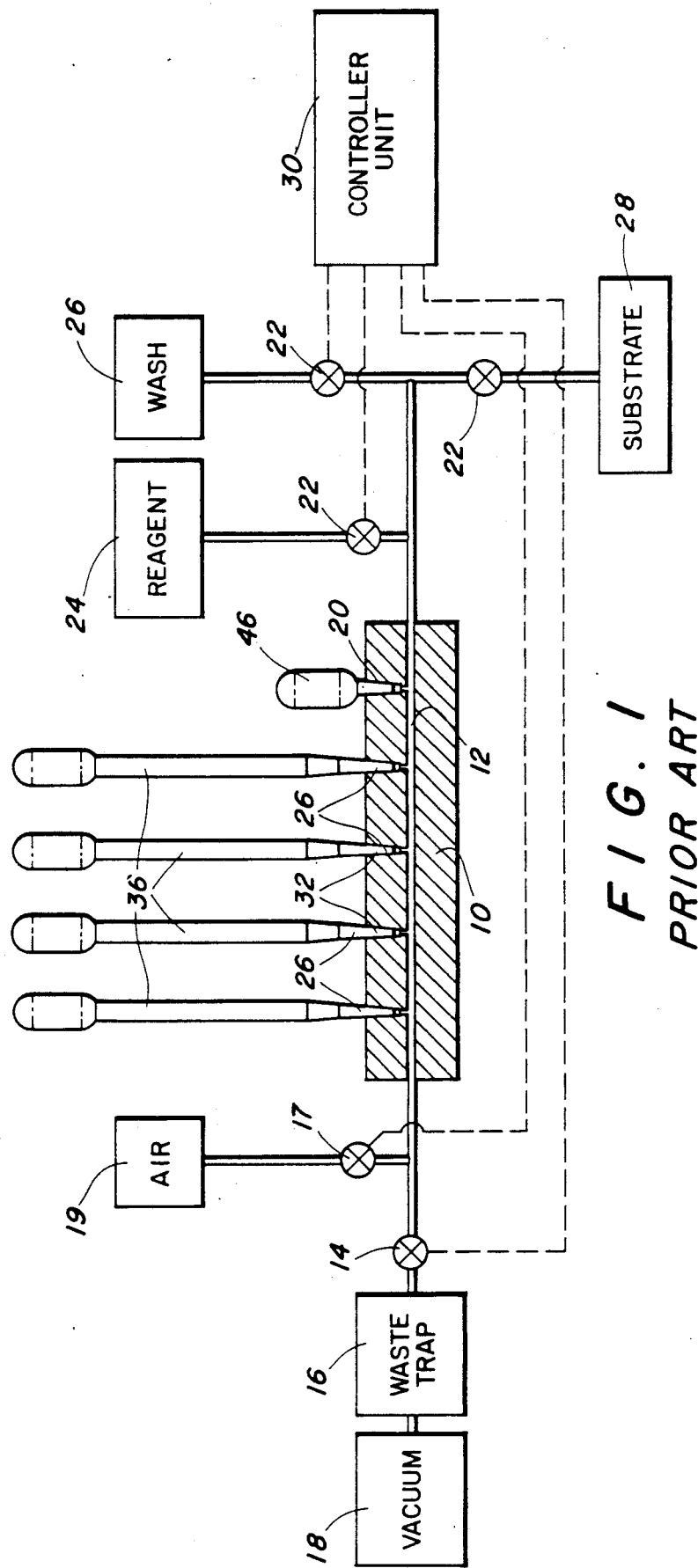
Figure 2:
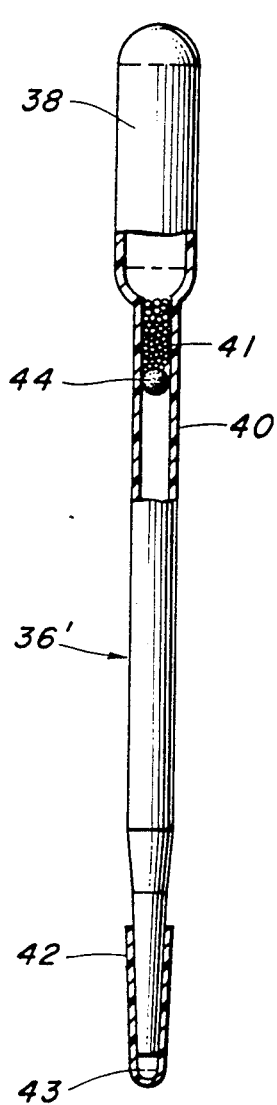
FIG. 2 is a pictorial view, partially cutaway of receptacle constructed in accordance with one embodiment of this invention for use with the system of FIG. 1.
Figure 3:
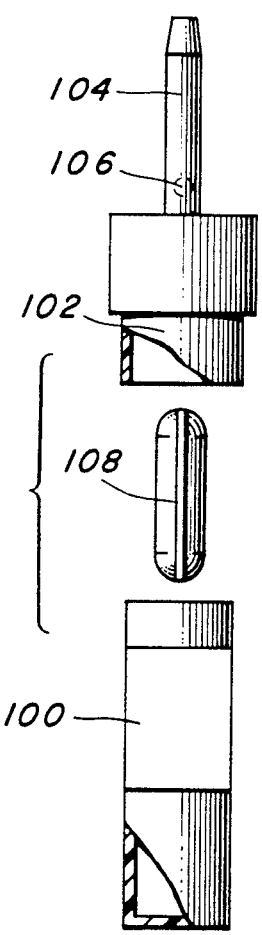
FIG. 3 is an exploded view of another form of receptacle that may be used with the system of FIG. 1.
Figure 4:
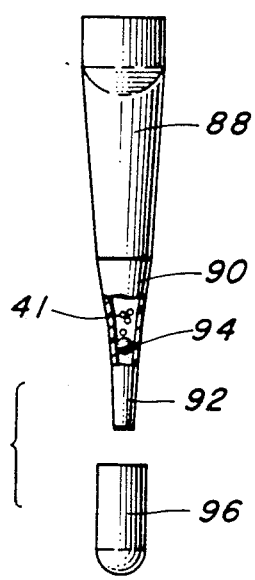
FIG. 4 is an exploded view of still another receptacle that may be used with the system of FIG. 1.
Figure 5:
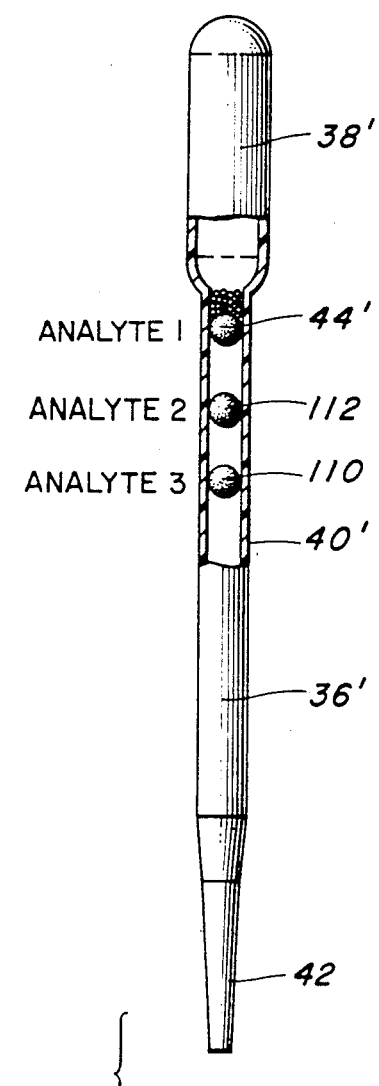
FIG. 5 is a pictorial view partially cutaway of still another receptacle that may find use with the system of FIG. 1.

A typical receptacle that may find use with the manifold of FIG. 1 is seen in FIG. 2 to be in the general form of a pipette having a bulbous upper portion or chamber 38 and an extended tubular portion 40. The receptacle may be formed of any of the plastic materials used for the manifold. Preferably the top bulbous portion 38 is flexible and joins the extended tubular portion 40 which is terminated in a tapered tip portion 42 which can be inserted in the taper of the manifold ports 32.

The upper chamber 38 provides a means of manually metering the fluid flow in and out of the receptacle. When and if the receptacle is used manually, by application of finger applied pressure, the user can control the amounts of sample and liquid reagents taken in and out of the receptacle. For example, test fluids may be drawn up to a precalibrated mark on the wall of the tube. In this way a measured amount of sample can be taken into the receptacle without the need for additional measurement apparatus. The upper chamber can be used for capture reagent storage. In addition, other types of reagents, i.e., antibody enzyme conjugates or other types of tag reagents may also be stored in this portion of the device. A porous retainer may be inserted into the tubular portion 40 retainer of the receptacle to function as a permeable barrier. The pores in the retainer may be large enough not to restrict fluid flow or the entrance of cells, microorganisms, cellular fragments or particulates of interest for analysis. On the other hand the pores may be small enough to efficiently collect the particulate capture reagents. In this way the capture reagents can be efficiently retained and washed. Thus, prior to inserting porous retainer 44 into the tubular portion 40 of the receptacle, particulate capture reagents 41 are introduced into the upper chamber compartment 38. In accordance with one particularly advantageous mode, it is desirable to combine the functions of the porous retainer and the capture absorbent. This can be achieved by immobilizing capture reagents such as an antibody for APS reductase on the porous retainer or onto the walls of the column tube itself. The capture reagent is immobilized by attachment to a solid support so that it cannot leave the receptacle.

The length of the tubular portion 40 together with the internal diameter of the tubular portion can create a volume which is equal to or less than that of the volume of the upper chamber compartment 38. Similarly the internal volume of the tubular portion 40 can exceed that of the sample of analyte such as the lysate of sulfate reducing bacteria and accompanying reagent fluids to be processed, i.e., the test fluid. Thus, the internal volume of the receptacle should exceed the volume of the test fluid by more than a factor of two.

In an alternative embodiment, the tubular portion 40 may be packed as a column. This approach provides a means of shaping the absorbent reagents into a microcolumn for capture of sample analyte. The column compartment can also function as a second reagent compartment. The capture or reagent particulates which have an antibody for APS reductase found thereon can be added during manufacture and stored in the column chamber. The column is formed simply by forming a porous plug (not shown) at either end of the column to retain the column packing.

In still other alternative embodiments, additional chambers can be added to the device. For example, crushable ampules or blisters can be integrated in the bulb 38. In this way the reagents can be compartmentalized until the appropriate step of the testing procedure. By application of pressure the ampules or blister parts could be opened for reagent delivery.

A protective cap 43 may be inserted over the end of the receptacle if desired for reagent protection during shipment or for user protection in handling devices during testing. For example, the protective cap can be used to provide an effective moisture barrier to protect dry reagents inside the receptacle during transportation and storage. During processing it may be desirable to make use of the cap to reduce user contact with sample materials which may be contained within the receptacle. Furthermore, the cap may be used to seal color formation reagents within the receptacle following testing, preventing them from leaking out during the color formation processes. The cap may be made of flexible chemically inert plastics similar to those described for the receptacle itself.

A plug 46 having a shape corresponding to the shape of the ports 32 may be used to close any manifold ports not occupied by a receptacle during test operations. The plug 46 may be formed of a suitable plastic of the same material as the receptacles.

The operation principle depends on the formation of a closed system created by inserting the fluid receptacles into ports of the multiport manifold. This forms a closed system involving coupling the interior of the manifold and the interior of the receptacle or test device. Coordinated opening of the vacuum and air valves enable the operational pressure within each receptacle to be reduced or increased to atmospheric pressure. Coordinated opening and closing of the reagent, air, vacuum, substrate and wash fluid valves provides fluid access to each receptacle. Preferably, the vacuum and air are applied in pulses. The same operational force can be used to remove the fluids from the receptacles.

On application of vacuum, air or gas retained within or added to the receptacle expands providing an expansion bubble which facilitates the removal of fluid from the receptacle by "pumping" the fluid out of the receptacle. By this means two directional fluid communication can be achieved in and out of the receptacle device by application of single directional vacuum force.

Fluid flow is thus achieved without the need for complicated equipment such as syringes or fluid pumps. In this way the system can be run at negative pressure. Thus fluids can be moved rapidly in both directions in and out of the receptacles through this single port by simple application of vacuum. Coordinated pulses of vacuum and air provides both the agitation of the solid phase capture reagents within the receptacle and provides a means of "active" analyte capture. Control over the vacuum in the manifold enables the sample and test reagents to be recycled back and forth through the reagent. This increases both the rate of analyte binding and maximizes the efficiency of analyte capture by the solid phase support. For example, the recycling process can be continued until the analyte in the sample is efficiently bound to the support. This capability not only reduces analysts time but also assures maximum testing response.

Figure 6:
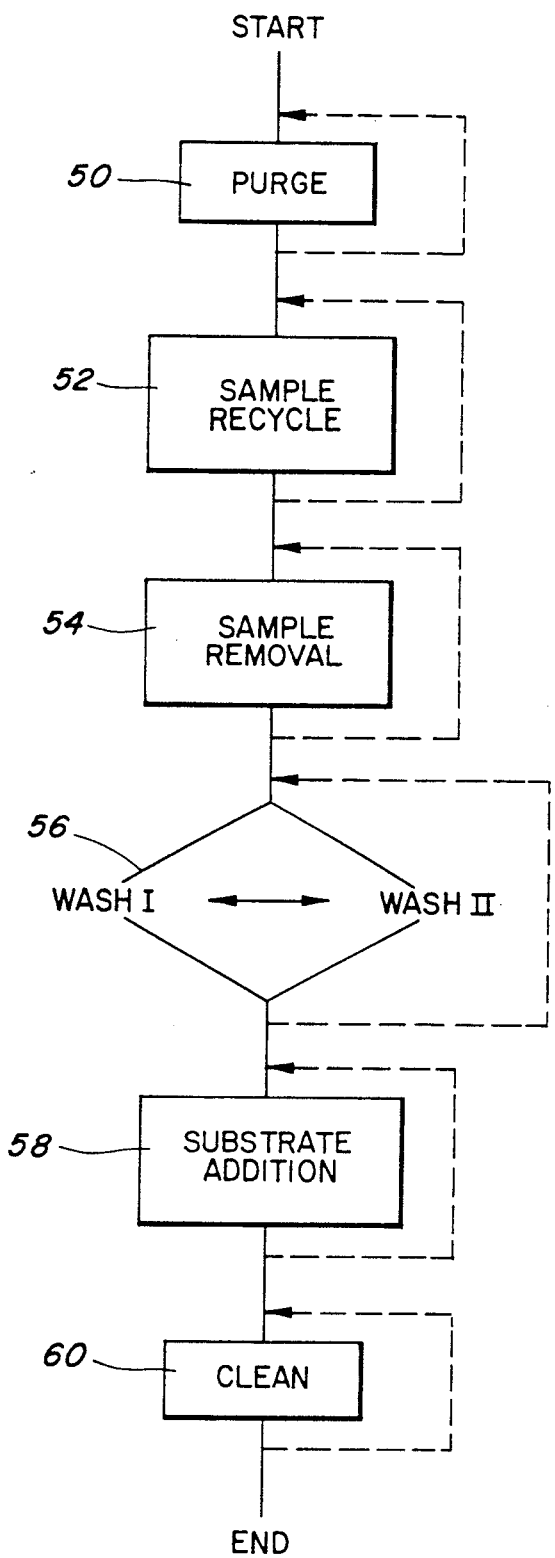
FIG. 6 is a flow diagram depicting the computer controlled method by which a complexation test is performed using the system of FIG. 1.
Figure 7:
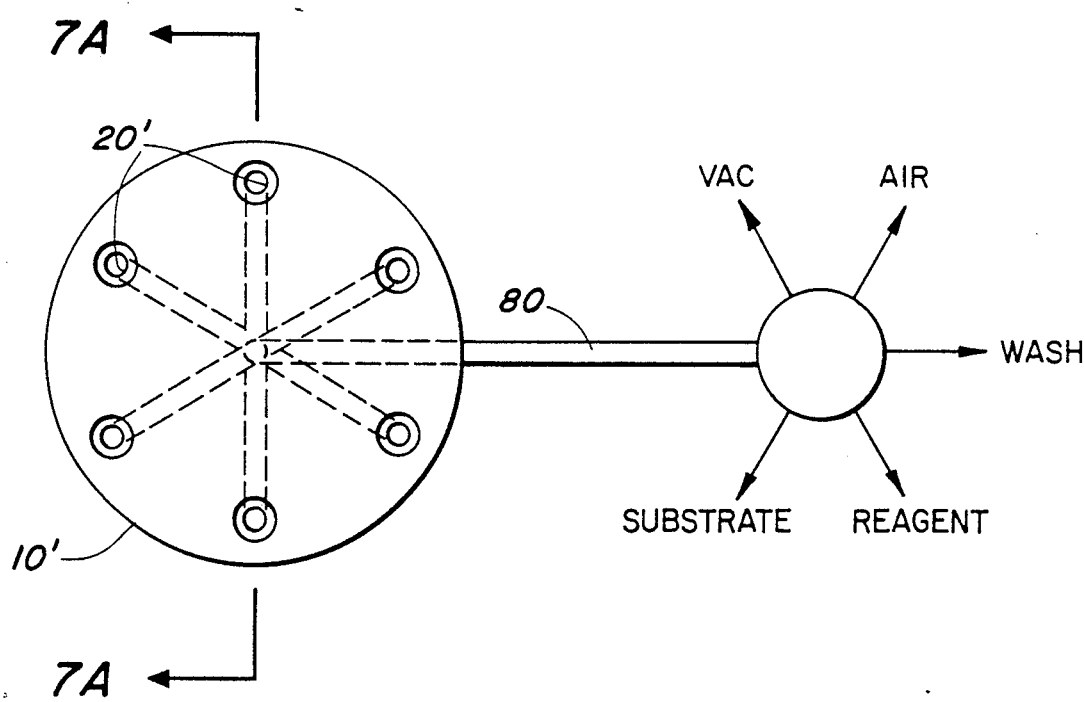
FIG. 7 is a partial pictorial, partial schematic view of an alternative form of manifold that may be used with the system of this invention.
Figure 7A:
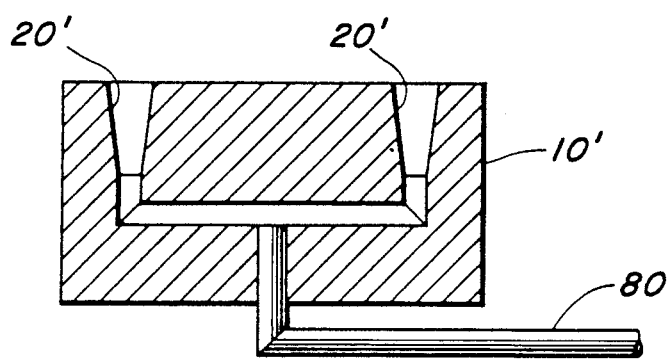

There may be seen in FIG. 6, a general processor program flow diagram by which the controller unit 30 (FIG. 1) actuates the various valves 14, 17, 22 (FIG. 1) to subject the receptacle 36 to vacuum or gas pressure or various wash or reagents. The program includes initially purging the system, as depicted by block 50, to clean the system before use. In this cycle, all of the ports 32 will be stoppered with a receptacle port plug 46 so that the system is closed. During the purge cycle, initially a vacuum from source 18 is applied to the conduit 12 as by opening the valve 14 for a period of time which may be in the order of 5 seconds. Immediately thereafter the valve 22 for the wash solution is opened with the vacuum for a short period of time, typically 0.2 second. During this portion of the cycle, wash fluid is drawn into the conduit 12 and out though the waste trap 16 to the vacuum source 18 thereby thoroughly cleansing the conduit. This cycle may be repeated several times, typically three times, during which vacuum is initially applied followed by the opening of valve 14 with one of the wash valves. Thereafter, the vacuum may be maintained for a short period of time to remove all liquids from the system, typically two seconds, after which the operator is given a pause command instructing him to place the receptacles into the device before proceeding further. During this pause, the receptacles 36 each containing a sample to be processed and a capture reagent capable of undergoing some type of complexation reaction that is, a reaction to form a complex, are placed in a different port 32.

Next, as depicted by block 52, the sample recycle sequence begins. During this sequence, the test fluids in the receptacle are forced successively through the capture reagent into the tubular portion of the receptacle and then back into the bulbous compartment 38 within the receptacle. This sequence is repeated 5-10 times to affect effective interaction of the sample with the capture reagents. This process is accomplished by initially applying an increasing gentle vacuum through valve 14 and opening the air valve 17 simultaneously. The valves are then closed. After a short delay, ca. 0.5 seconds, the air valve 17 is opened for typically 5-10 seconds. This allows test fluids to flow back into the top of the receptacle. The vacuum/air valve sequence, described above, is then repeated typically 3-10 times, until effective analyte capture has been accomplished. During processing, it is important to leave some gas or air in the receptacle so that fluid may be later withdrawn as will be described below.

Next, as depicted by block 54, the sample is removed from the receptacle and passed to the waste trap 16. This must be accomplished while avoiding sample transfer between receptacles. Typically this is carried out by gradually removing the fluids from the receptacle and diluting the test fluids in the manifold chamber 10 as they are swept to the trap. Procedurally, the pressure with the receptacles is progressively reduced by repeatedly opening simultaneously the vacuum and wash valves for 0.1 second intervals. This gradually reduces the pressure within the receptacle while pulling wash fluids through the manifold to dilute and sweep the fluids into the trap 16. The sample removal cycle is then completed by application of a stronger vacuum to remove all residual fluids by repeatedly opening vacuum valve 14 for 0.5 second intervals.

Next, the receptacle can be washed as depicted at 56 (FIG. 6). During the wash cycle, the receptacle is subjected to vacuum by opening valve 14 for typically 5-10 seconds. Thereafter, wash fluids are injected by opening valves 19 and 22. This permits the receptacles to be filled with wash fluid. The fluid is then removed in stages by successively applying vacuum and then air to the manifold system. This alternate addition of vacuum and air distributes the fluids and suspends the capture reagents within the receptacle, this agitation ensures that all internal surfaces are contacted by fluid. The alternate addition of vacuum and air is repeated several times. Finally, vacuum is applied to remove any remaining fluid in the receptacle. During this phase, trapped gas within the receptacle expands—forcing the fluid from the receptacle. The addition of air thus contributes both to increased wash efficiency and removal of fluid from the manifold system.

Next, a color formation reagent such as a proteinaceous material capable of being recognized by development of color and a color development agent, either together or sequentially is added (block 58) to each receptacle 36 by first subjecting the entire manifold system to vacuum. Next, the substrate reagent 28 (FIG. 1) is added followed by the application of air pressure to suspend the capture particulates and force the color formation reagent into the receptacles 36. This pulsed application of air is repeated several times after which air is applied for about 10 seconds. A delay of several minutes is interposed to allow color development to take place and the receptacles to be "read". Thereafter the system is cleaned (block 60) by the application of vacuum followed by alternate pulses of washing solution, and vacuum. This sequence of wash solution and vacuum is repeated several times.

By selectively subjecting the receptacle to reagents, air, wash fluids and vacuum, fluid flow into and out of the device is precisely controlled and all of the essential procedural functions required for complexation processes, that is, processes to form complexes, can be achieved. Full automation of a test method is thus achieved.

The important testing advantages realized as a result of the system and method of operation, such as accelerated test response and high sensitivity, can also be achieved by using the test receptacles in a manual mode. The flexible, bulbous receptacle of this invention enables the fluids to be drawn into the device and processed manually. Thus the testing functions of sample metering, active analyte capture, reagent separation, and additional color formation reagents can be carried out manually by user application of finger force on the collapsible, bulbous receptacle. During this process, active analyte capture is also achieved by recycling the sample back and forth through the capture agent. Excess sample and reagents can then be removed and separated from the "bound" analyte by subsequent wash steps. Bound analyte can then be detected using either non-isotopic and/or isotopic-tagged reagent. The bulbous receptacle thus can perform many of the functions of both a pipette and dropper. Although the testing advantages of testing speed and sensitivity achieved with this system are retained during manual operation, the manual procedures require active operator participation and therefore is more labor intensive and subject to operator errors.

PREFERRED EMBODIMENTS OF THE INVENTION

Some presently preferred embodiments of the invention have been particularly described in the preceding section in connection with the Detailed Description of the Drawings. Other presently preferred modes are hereinafter described, and further elaboration is provided.

In a basic embodiment, the invention relates to a method for detecting sulfate-reducing bacteria in an aqueous environment comprising three essential steps. In the first step, a sample taken from the environment and selected so as to include microbes present in the environment is lysed so as to release into the lysate an enzyme which the sulfate-reducing bacteria utilize to derive energy by reduction of the sulfate. The sample can be taken by any conventional technique. For example, if the environment to be assayed is aqueous liquid in a well bore or a subterranean hydrocarbon containing formation, the liquid can be simply produced by means of a rod pump, swabbing the well bore, or the like, and samples taken from the produced liquid. In accordance with another example, if the environment is found beneath bacterial colonies growing on metal surfaces such as welds, in pipes, on cooling towers, or in reaction vessels, representative examples of the colonies can be scraped into an aqueous liquid and broken up, conveniently as part of the technique for preparing the lysate. If the bacteria comprise a relatively small portion of the sample, they can readily be concentrated by known techniques, for example, filtration, centrifugation, and the like. If a quantitative or semi-quantitative determination of the number of sulfate-reducing bacteria is desired, attention should, of course, be paid to keeping track of aliquots in dilution or concentration steps.

Once a sample is taken from the environment and suitably concentrated, diluted, and/or otherwise prepared, the lysate is prepared by any suitable technique known to the art. For example, the cell walls can be lysed or ruptured by mechanical agitation, ultrasonics, enzyme or other chemical attack of the cell walls, or the like. Care should, of course, be taken that the methods for carrying out the lyses do not result in denaturing the enzyme which the sulfate-reducing bacteria utilize to derive energy by reduction of sulfate. Presently, sonic lysis is a preferred technique, and has been found to be both convenient and effective.

The enzyme which the sulfate-reducing bacteria utilizes to derive energy by reduction of sulfate which is released and which the method takes advantage of is presently preferably an adenosine 5'-phosphosulfate reductase, for short, APS reductase, but without deterring from the generality of the invention. Other reductases such as the sulfite reductases may also be suitable.

In the second step of the method for detecting sulfate-reducing bacteria, a portion of the lysate prepared in the first step is contacted with an antibody for the enzyme under reactive conditions for an antibody-enzyme reaction.

The antibody for the enzyme can be prepared by conventional techniques. For example, the preferred APS reductase can be purified of other proteinaceous material by conventional biochemical techniques and thereupon injected into an organism having an immune system. Conveniently, laboratory animals such as rabbits, mice, rats, and the like can be used as a suitable organism having an immune system, or for large quantities, larger animals such as goats, sheep, cattle, and horses can be considered. Rabbits have been found to be convenient for the practice of the invention to date. In accordance with one mode, the purified APS reductase is injected into the animal's blood stream, and antibodies are harvested after they have been formed by the animal's immune system. The antibodies are conveniently recovered and purified by conventional techniques.

In the second step, the suitably isolated antibody and the aqueous liquid potentially containing the enzyme are contacted under reactive conditions for an antibody-enzyme reaction. Here again, conventional immunological techniques are employed, and generally the antibody-enzyme reaction takes place in an aqueous environment at ordinary room temperatures, though other conditions can be employed so long as the enzyme and antibody proteins are not denatured.

Further in accordance with this presently preferred embodiment of the invention, the reaction product of the enzyme and the antibody is detected so as to determine the presence of the sulfate-reducing bacteria in a unique fashion. Most simply, the reaction product can under some circumstances be detected visually because of agglutination which takes place. However, other means of detection can be employed, for example, by adding a known quantity of radioactively tagged enzyme to the enzyme sample assayed and then measuring radioactivity of the reaction product, by measuring the absorbance, reflectance, or fluorescence induced by radiation impinged upon the reaction product, or by other techniques that are known to the art.

Presently, the reaction product is preferably detected by contacting the exemplary reacted antibody-APS reductase reaction product with a proteinaceous material capable of being readily recognized by development of color to form a complex, and then developing the color of the complex thus formed. Suitable detection techniques are more specifically disclosed in the examples of this application. Other suitable techniques are known to the art or will readily suggest themselves to those skilled in the art. For example, the proteinaceous material can be tagged with a radioactive isotope, it can be tagged with a moiety which is readily detectable by absorption, reflectance, or fluorescence, or it can contain a moiety that is readily detectable by nuclear magnetic resonance (NMR) or the like, to provide merely some example of the methodology that can be employed.

It should be understood that the sequence of steps is not necessarily critical. Thus, in an exemplary procedure, the antibody can be reacted with the APS reductase, which then is reacted with a proteinaceous material capable of forming a complex which is recognized by development of color, and then the color can be developed by means of a suitable reactant such as a peroxide. It is also feasible to react the APS reductase with a proteinaceous material containing for example peroxidase and thereupon react the complex with the antibody. Furthermore, it is feasible to conduct both sequences concurrently. Thus, in one presently particularly preferred embodiment, the antibody is linked to a solid substrate in a suitable container. The lysate containing the APS reductase is then introduced into the container, and part of it reacts with the antibody which is linked to the solid substrate. Another portion of the APS reductase remains unbound. Proteinaceous material capable of forming a complex which is recognized by development of color and material capable of developing the color are pre-introduced or introduced in any other sequence into the container. Part of the APS reductase reacts with the proteinaceous material which then reacts with the antibody, and the color developing material develops color, all reactions taking place in the container. Assay for the APS reductase and consequently the sulfate-reducing bacteria is determined by the presence and/or intensity of color associated with the peroxidase containing proteinaceous material linked to the solid phase support by way of the antibody linked onto the solid phase support. Of course, the reactive materials can be added sequentially with appropriate washing between materials as well.

In accordance with one presently preferred embodiment, a solid support is disposed in a suitable container. The solid phase support comprises, for example, polystyrene which is reacted with a monomer solution having a grafting site and an antibody attachment site. The grafting site can be, for example, a suitably activated ethylene moiety and the antibody attachment site, for example, can be an epoxy moiety. One example of a suitable monomer is glycidyl methacrylate. Other suitable materials are known or will readily suggest themselves to those skilled in the art. More specifically, in accordance with one presently preferred embodiment, polystyrene beads are reacted with glycidyl methacrylate in the presence of an electron beam to form a surface graft polymer having a plurality of epoxy groups, such as a polystyrene-poly (glycidyl methacrylate) graft polymer. An antibody for an enzyme which sulfate-reducing bacteria utilize to derive energy by reduction of sulfate can then be linked with the surface graft polymer having an antibody attachment site such as the polyglycidyl methacrylate having a plurality of epoxy groups. Exemplary antibodies prepared by injecting APS reductase from sulfate-reducing bacteria into an organism having an immune system can be linked onto a polyglycidyl methacrylate surface graft polymer wherein the graft is onto polystyrene beads, and the resultant material can be disposed in a container having an access port and a means for introducing and removing liquids from the container. In accordance with this presently preferred embodiment, it is also often convenient to situate a proteinaceous material capable of being readily recognized by development of color in the container as well as a material capable of developing the color of the proteinaceous material. Various other configurations will suggest themselves to those skilled in the art in view of this disclosure. For example, in a relatively simple configuration, the solid support, in the form of beads or other shaped configurations can be situated along with the other materials in an ordinary pipette, and the lysates to be tested and other materials can be introduced by means of suction, or the like.

A sophisticated mode was heretofore described with reference to EPA Application 0198413. However, for ordinary field assay and control of sulfate-reducing bacteria, one of the more simple modes heretofore described may be more practical in many circumstances.

In accordance with a presently preferred mode, the sulfate-reducing bacteria can be detected in a qualitative sense, or by appropriate attention to keeping track of aliquots and suitable calibration, the sulfate-reducing bacteria can be both detected and quantified with respect to the aqueous environment.

In accordance with another presently preferred embodiment of the invention, an effective amount of a bactericidal or bacteriostatic agent for sulfate-reducing bacteria is introduced into the aqueous environment responsive to the presence of the sulfate-reducing bacteria so as to kill or inhibit the growth of the sulfate-reducing bacteria detected in the aqueous environment. Two advantages of the detection method for control are 1.) it yields data on the presence of sulfate-reducing bacteria very rapidly in comparison to current methods, in a few minutes compared to current methods which may require weeks for data acquisition and 2.) the inventive method is far more sensitive, which allows detection of very low levels of bacteria. The consequences of this for control are that biocides may be administered when cell densities are low enough to (a) be susceptible to biocides and (b) be inhibited by low biocide doses thus resulting in a cost savings. This contrasts with the current situation where weeks elapse between water sampling and the test results. Since sulfate-reducers like most bacteria reproduce very rapidly and may have a doubling time in the natural environment of 10–20 hours, a two week incubation time allows the growth of bacterial densities which may not respond to biocide treatment. Additionally, the effectiveness of a particular biocide may be rapidly evaluated which can result in lower biocide usage. Preferably, the control measures are tailored to the quantity of sulfate-reducing bacteria detected. They are also tailored to the particular environment. For example, in the case of sulfate-reducing bacteria found between corrodible materials and colonies of other bacteria, use of ozone, hydrogen peroxide, or other peroxides can be employed. For example, if the sulfate-reducing bacteria are causing deleterious effects in a bore hole or subterranean formation, organic biocides can be employed. A number of suitable biocides are known in the industry including acrolein, chlorine, aldehydes such as formaldehyde, chlorates, quaternary ammonium salts, and the like. An advantage of this preferred embodiment of the invention is that the control measures can be tailored to the presence and quantity of sulfate-reducing bacteria present. Thus, wasteful and expensive treatments which may introduce deleterious materials into the environment can be avoided.

In accordance with one particularly preferred mode of this embodiment, an assay for sulfate-reducing bacteria can be run after bactericidal or bacteriostatic treatment of the environment has been effected so as to determine the effectiveness of the treatment and the possible need for further treatment.

EXAMPLES

The following examples are provided in order to more fully explain the invention and provide information to those skilled in the art on how to carry it out. However, it is to be understood that these examples are not intended to function as limitations on the invention as described and claimed herein.

A presently preferred mode is exemplified in Examples 1-7, following. The following procedure was employed:

An exemplary strain of *Desulfovibrio desulfuricans* was isolated from production well water obtained at a Conoco Inc. lease site, designated Grubb Lease Well #100, located at Ventura, Calif. The strain used was isolated by picking a single colony twice in serial succession from Supplemented BTZ-3 medium. Microbial characterization determined the isolate to be *D. desulfuricans*.

BTZ-3 medium has the following composition:

| | |
|---|---|
| $NH_4Cl$ | 4.3 g |
| $KH_2PO$ | 0.5 g |
| $MgCl_2.6H_2O$ | 0.2 g |
| Na acetate | 2.0 g |
| $CaCl_2.2H_2O$ | 0.1 g |
| Yeast Extract | 0.85 g |
| Distilled $H_2O$ | 840 mL |
| Mineral solution | 10 mL |

Composition of the mineral solution:

| | |
|---|---|
| Nitrilotriacetic acid | 6.4 g |
| $FeCl_2.4H_2O$ | 150 mg |
| $CuCl_2$ | 10 mg |
| $MnCl_24H_2O$ | 50 mg |
| $CoCl_2$ | 85 mg |
| $ZnCl_2$ | 50 mg |
| $H_3BO_3$ | 5 mg |
| $Na_2MoO_4.2H_2O$ | 5 mg |
| $H_2O$ | 500 mL |
| Adjust pH to 7.0 | |

Supplemented BTZ-3 medium was prepared by adding aliquots of filter sterilized solutions of Na lactate and Na sulfate so that each is present at a final concentration of 40 mM. For solid medium, 1.2% (by weight) agar was added to Supplemented BTZ-3 medium. Yeast Extract was obtained from Difco Laboratories, Detroit, Mich.

*D. gigas, D. vulgaris, D. desulfuricans* (Norway), *D. multispirans, Desulfosarcina variablis, Desulfotomaculum ruminis, Dt. orientis, D. desulfuricans*, strain 27774 were obtained from the laboratory of Dr. H. D. Peck, Department of Biochemistry, University of Georgia, Athens, Ga., 30601. *D. desulfuricans* strain API was obtained from the American Petroleum Institute. These sulfate-reducing bacteria were grown in flasks containing 500 mL of Supplemented BTZ-3 medium under an argon atmosphere.

Colorless sulfur bacteria, *Thiobacillus thioparus* ATCC 8158, *T. denitrificans* ATCC 23642, and *T. neapolitanus* ATCC 2308, and *T. ferrooxidans* ATCC 23270 were obtained and grown on the media recommended by ATCC. They were grown in cultures containing 200 mL of medium under aerobic conditions with shaking.

Photosynthetic sulfur bacteria, *Chlorobium thiosulfatophilum* ATCC 17092 and *Chromatium vinosum* ATCC 17899 were obtained and grown on the media recommended by ATCC. They were grown photosynthetically and anaerobically in wheaton bottles containing 200 mL of medium.

*Escherichia coli* HB101 was obtained from J. D. Wall, Department of Biochemistry, University of Missouri, Columbia, Mo., 65201. They were grown in cultures containing 200 mL of medium under aerobic conditions with shaking.

*Streptomyces lividans* strain J1326 was obtained from the John Innes Institute, Norwich, United Kingdom. They were grown in cultures containing 200 mL of medium under aerobic conditions with shaking.

COLLECTION AND LYSIS OF BACTERIAL CELLS

Bacteria from the various cultures were collected by centrifuging the bacterial suspensions for 30 min at 10,000 rpm in a Sorvall GSA rotor. The resulting sediments of bacteria were resuspended (1:10 wt/vol) in 25 mM Hepes (hydroxyethylpiperazine ethanesulfonate, purchased from Sigma Chemical Co., St. Louis, Mo.) buffer at pH 7.0 and passed through a French pressure cell under 20,000 psi. The resulting cell lysate was centrifuged for 30 min at 15,000 rpm in a Sorvall SS-34 rotor to sediment unbroken bacterial cells. The supernatant fluid contained the soluble proteins and particulate membrane fragments. Supernatant fluids from cultures of the various bacteria, appropriately diluted in Phosphate Buffered Saline pH 7.2 (PBS) (sodium chloride, 8.0 g, potassium chloride, 0.2 g, di-sodium hydrogen phosphate, 0.2 g, water, 1000 mL) served as the samples subjected to immunological analysis for APS reductase. The Following Technique for Preparation and Purification of APS Reductase to Serve as the Antigen for Antibody Production was Employed.

The sedimented bacterial cells (50 g) from a culture of *D. desulfuricans*, strain G100A were suspended (1:2 wt/vol) in 25 mM Tris buffer solution (100 mL) with a pH of 7.0. The resulting suspension was passed through a French pressure cell as indicated above. The resulting lysate was centrifuged as described above then the resulting supernatant fluid was centrifuged for an additional 90 min at $180,000 \times g$. Streptomycin sulfate (35 mL of a 5% solution) was added to the resulting supernatant fluid to precipitate the nucleic acids. The precipitated nucleic acids were sedimented by centrifugation at $20,000 \times g$ for 20 min. The resulting supernatant fluid contained only soluble proteins and was designated the crude extract.

Step 1. Ammonium Sulfate Fractionation: Ammonium sulfate was added to the crude extract to a concentration 35% (by weight) of the saturated concentration. The resulting precipitate was collected by centrifuging the mixture at $20,000 \times g$ for 20 min. More ammonium sulfate was added to the resulting supernatant fluid to a concentration of 60% of saturation and the precipitate collected after centrifugation as above. The two precipitates recovered were dissolved in 50 mL of Tris-HCl buffer pH 7.0 and assayed for APS reductase activity as described herein. The majority of the activity was found in the precipitate recovered when the ammonium sulfate was brought to 60% of the saturation concentration.

Step 2. Phenyl-sepharose Chromatography: Ammonium sulfate was added to the dissolved precipitate from the 60% fraction from Step 1 to a final concentration of 1M. This solution was added to a phenyl-sepharose column (2.5 cm $\times$ 20 cm) (Sigma Chemical Co., P.O. Box 14508, St. Louis, Mo. 63178) which had been equilibrated with 1M ammonium sulfate solution in 25 mM Tris-HCL buffer, PH 7.0. After the protein had been completely absorbed onto the column, the proteins were eluted with an ammonium sulfate gradient from 1M to approaching 0M in 25 mM Tris-HCl buffer, pH 7.0. This step resulted in nearly three-fold purification with the recovery of 63% of the enzyme activity.

Step 3. Hydroxyl Apatite Chromatography: Sodium chloride was added to the solution containing the eluted proteins from Step 2 to a concentration of 0.3M and the resulting solution was added to a hydroxyl-apatite column (2.5 cm×10 cm) (Bio-Rad Laboratories, 2200 Wright Avenue, Richmond, Calif.). The proteins were first eluted with 25 mM Tris-HCl buffer, pH 7.0. This eluate contained 30% of the total APS reductase and subsequent electrophoresis showed it to be essentially homogenous. The remaining APS reductase was step eluted with 10 mM phosphate buffer, pH 7.0. The first and second fractions were combined and applied to a small Diethylaminoethyl 52 cellulose column (1 cm×3 cm) (Whatman Ltd., Maidstone, England) for concentration to approximately 5–6 mL in 25 mM Tris-HCl buffer, pH 7.0 which was 0.4M with respect to sodium chloride.

Step 4. S300 Gel Filtration Chromatography: The concentrated APS reductase from Step 3 was applied to an S300 column (2.5 cm×90 cm) (Bio-Rad Laboratories) equilibrated with 25 mM Tris-HCl buffer, pH 7.0. Solution was pumped through the column at a rate of 15 mL per hour. The eluted APS reductase was purified almost two-fold relative to the material recovered after Step 3, and the total recovery of enzyme activity was 21%.

At each step in the purification, the amount of protein was determined by the method described by Lowry et al., J. Biol. Chem., 193: 265 (1951) and the amount of APS reductase was determined. APS reductase activity was assayed by spectrophotometrically monitoring ferricyanide reduction at 420 nm ($E_M = 1000$) in the presence of sulfite and adenosine 5'-monophosphate (AMP). Typically, 10–100 μL of enzyme extract was added to a 3 mL reaction mixture consisting of 2 mM potassium ferricyanide, 0.33 mM AMP and 100 mM Tris buffer at pH 7.5. The reaction is started by the addition of 100 μL of 0.1 sodium sulfite in 5 mM EDTA (ethylene diamine tetraacetic acid). The results of this purification are shown are shown in Table 1.

TABLE 1

| Step No. | Volume (mL) | Units/mL* | Total units | Protein (mg/mL) | Units/mg protein |
|---|---|---|---|---|---|
| 0 | 120 | 13.2 | 1590 | 36.6 | 0.36 |
| 1 | 63 | 17.8 | 1123 | 25.0 | 0.71 |
| 2 | 50 | 14.3 | 712 | 7.0 | 2.0 |
| 3 | 73 | 6.0 | 438 | 3.0 | 2.0 |
| 4 | 30 | 11.2 | 330 | 2.9 | 3.9 |

*Units = O.D at 420 nm/min

The purification procedure resulted in a 21% recovery of enzyme activity with a purification of 10.7 fold. Polyacrylamide gel electrophoretic analysis of the resulting product indicated the presence of a single species of protein with a molecular weight of 132,000 daltons when the electrophoresis was carried out under native conditions and the same analysis indicated two proteins with molecular weights of 75,000 and 25,000 when the electrophoresis was carried out under denaturing conditions. The enzyme is considered pure.

Two rabbits were immunized against the resulting purified enzyme protein by injecting them with the protein in a suitable carrier according to an injection schedule and by routes well known to immunologists. Serum, (pre-immune sera) to serve as control sera in later immune testing, was removed from the rabbits prior to their receiving injections of enzyme protein. The specificity and selectivity of the antibodies for APS reductase is a key component of this invention. While the antibodies in the examples given below were produced by injecting rabbits with purified APS reductase from *D. desulfuricans*, strain G100A, purified APS reductase from any of the sulfate-reducing bacteria are believed to suffice to serve as antigen for the production of the antibodies and immune serum from any animal suitable for the production of antibodies are believed to suffice.

EXAMPLES 1–7

The enzyme-linked immunosorbent assay procedure used was that described in "Laboratory Techniques in Biochemistry and Molecular Biology: Practice and Theory of Enzyme Immunoassays". P. Tijssen, eds. R. H. Burdon, P. H. van Knippenberg, Elsevier, pp 335–336. The ability of both pre-immune and immune sera to react with proteins in sulfate-reducing bacteria was tested as follows. Crude extract, as defined above, containing 800 ng of protein from each bacterial strain was added to each of two wells of a microtiter plate (Nunclon, obtained from Gibco, Life Technologies, Inc., Grand Island, N.Y., 14072). After two hours of incubation at 25° C., the wells were washed four times with an excess of phosphate buffered saline PBS buffer containing 0.05% Tween 20 surfactant (Sigma Chemical Co.) and 0.5% by weight of gelatin. The washing removes unattached antigen and prevents any additional binding of protein to the plastic in the wells. A 200 μL aliquot of pre-immune or immune serum diluted 1000 fold in PBS buffer, was added to the appropriate wells and incubated for 2 hr at 25° C. The wells were then washed four additional times with PBS containing 0.05% by weight of surfactant TWEEN and 0.5% gelatin. A second antibody solution which consists of anti-rabbit IgG conjugated to peroxides (Sigma Chemical Co.) was diluted 1000 fold with PBS buffer, applied to each well (200 μL) and incubated for 2 hr at 25° C. Each well was again washed with PBS containing TWEEN and gelatin to remove excess conjugated antibodies. An aliquot (200 μL) of peroxidase substrate containing solution was added to each well. The peroxidase substrate solution which is freshly prepared for each use consisted of 0.15M citrate-phosphate buffer pH 5, 100 mL, o-phenylenediamine hydrochloride, 34 mg, 30% hydrogen peroxide solution, 50 μL. Within 10 minutes, the optical density at 410 nm was recorded using a Dyna-Teach microtiter plate reader. The results are shown in Table 2. The optical densities shown in the table for each bacterial sample tested were arrived at by subtracting the values obtained in the wells which were reacted with preimmune serum from the values from the wells receiving immune serum. The results demonstrating the ability of this antiserum prepared against purified APS reductase from *D. desulfuricans* G100A to react with purified enzyme from the same organisms as well as crude extracts from the same strain, three additional strains of the same species and two other species of the same genus are shown in Table 2.

TABLE 2

| Bacterial origin of sample | O.D.410 |
|---|---|
| purified APS reductase from D. desulfuricans G100A | 0.96 |
| D. desulfuricans strain G100A | 0.96 |
| D. desulfuricans strain API | 0.80 |
| D. desulfuricans strain 13541 | 0.75 |
| D. desulfuricans strain 27774 | 0.46 |
| D. gigas | 0.71 |
| D. vulgaris | 0.80 |

Strong reactivity is shown for all the samples tested.

COMPARATIVE EXAMPLES 8 AND 9

The purpose of these examples is to show that the immune serum prepared against purified APS reductase from D. desulfuricans strain G100A does not react with extracts from non sulfate-reducing bacteria.

Extracts as described above were made of cultures of Streptomyces lividans and Escherichia coli. They were reacted with pre-immune serum and immune serum and the amount of reactivity determined as described in Examples 1–7. The results are shown in Table 3.

TABLE 3

| Bacterial origin of sample | O.D.410 |
|---|---|
| S. lividans | 0.05 |
| E. coli | 0.02 |

Little or no reactivity resulted.

EXAMPLE 10

This example confirms that the material in the extracts that reacts with the immune serum is APS reductase and not some other protein and that the reactivity is not some non-specific reactivity. Western immunoblot analysis of extracts of three different species of Desulfovibrio and the purified APS reductase were done. Crude extracts of cultures of the bacteria were prepared as described above. Purified APS reductase was prepared as described above. The analysis consisted of the electrophoretic separation of the crude extracts followed by electroelution of the protein bands onto nitrocellulose paper essentially as described in the Bio-Rad Protein slab gel instruction manual (for electrophoresis) and the Bio-Rad Trans-Blot transfer media instruction bulletin (for electroelution), (Bio-Rad Laboratories). The species of Desulfovibrio tested were D. multispirans, D. desulfuricans strain API and D. desulfuricans strain G100A. The nitrocellulose containing the transferred proteins was incubated with a 1:1000 dilution of immune serum for 2 hr then with PBS containing TWEEN and gelatin for 30 min and then with the solution containing a 1:1000 dilution of anti-rabbit IgG conjugated with peroxidase for 2 hr. The nitrocellulose and proteins were finally stained with peroxidase substrate which develops a color wherever the conjugated antibodies are localized. D. desulfuricans strain API and D. desulfuricans strain G100A each yielded a single stained protein and both were coincident in their position on the nitrocellulose with the position of the purified APS reductase. Therefore, the antiserum contained antibodies only to APS reductase and the material from each of the other organisms tested contained APS reductase which reacted with the antiserum. The extract from D. multispirans also exhibited only a single stained protein but the position of this protein was not coincident with the positions of the others. Therefore, the antiserum against the APS reductase of D. desulfuricans strain G100A reacts with an electrophoretic variant of the enzyme. It was determined in an independent experiment that the protein detected in D. multispirans is APS reductase.

EXAMPLES 11–12

The purpose of these examples is to demonstrate the range of sulfate-reducing organisms which contain in their extracts proteins which react with the immune serum produced against the purified APS reductase of D. desulfuricans strain G100A. The extracts of the various bacteria were prepared as described in Examples 1–7. The testing differs in that three different concentrations of extract were added to the wells of the plastic testing plates. The concentrations of protein in the extract added to each of two wells was 600 ng, 60 ng, and 6 ng. The rest of the procedure was done as described in Examples 1–7. For control purposes, purified APS reductase, extract of D. desulfuricans strain G100A and a sample of an extract of the non sulfate-reducing S. lividans was included. The results are shown in Table 4.

TABLE 4

| Bacterial extract in sample | O.D.410 | | |
|---|---|---|---|
| | 600 ng | 60 ng | 6 ng |
| purified APS reductase from D. desulfuricans G100A | 1.6 | 1.3 | 0.8 |
| D. desulfuricans strain G100A | 1.3 | 1.3 | 1.3 |
| D. desulfuricans strain Norway | 0.7 | 0.4 | 0.2 |
| Dt. orientis | 1.1 | 0.6 | 0.5 |
| S. lividans | 0.3 | 0.1 | 0.2 |

These results show that when concentrations of 60 ng or more of protein in the extract was tested for the presence of immunoreactivity to an anti-APS reductase specific antiserum, an additional strain of the genus Desulfovibrio and one species of the genus Desulfotomaculum contained reactive material. The non sulfate-reducing S. lividans did not react significantly with the antiserum.

EXAMPLES 13–17

Species of the genera Thiobacillus, Chlorobium, and Chromatium, sulfide-oxidizing bacteria, are known to contain an APS reductase. The purpose of these examples is to show that extracts of these bacteria do not contain materials which show significant immunoreactivity to an anti-APS reductase specific antiserum. Extracts of cultures of these bacteria were prepared as described in Examples 1–7. The concentrations of protein in the extract added to each of two wells was 600 ng, 60 ng and 6 ng, as in Examples 11 and 12. The rest of the procedure was done as described in Examples 1–7. The results are shown in Table 5.

TABLE 5

| Bacterial extract in sample | O.D.410 | | |
|---|---|---|---|
| | 600 ng | 60 ng | 6 ng |
| T. thioparus | 0.0 | 0.1 | 0.1 |
| T. neapolitanus | 0.0 | 0.0 | 0.1 |
| T. ferrooxidans | 0.0 | 0.0 | 0.0 |

TABLE 5-continued

| Bacterial extract | O.D.$_{410}$ | | |
|---|---|---|---|
| in sample | 600 ng | 60 ng | 6 ng |
| Chromatium vinosum | 0.7 | 0.3 | 0.1 |
| Chlorobium thiosulfatophilum | 0.0 | 0.1 | 0.2 |

The extracts of only one of these sulfide-oxidizing bacteria contained material which reacted with the antiserum against the purified APS reductase of D. desulfuricans strain G100A. In another experiment, no cross-reactivity was observed when an extract of C. vinosum was assayed.

EXAMPLE 18

The purpose of this example is to show that a key element in practicing a presently preferred mode of this invention resides in recognizing APS reductase in bacterial extracts by determining the presence and amount of reaction product resulting from the reaction of APS reductase with specific antibodies in an antiserum produced against a purified APS reductase. Any assay that will reliably and conveniently detect the reacted APS reductase, anti-APS reductase antibody reaction product may be used. In this example, a different way of generating and measuring the said reaction product is demonstrated.

The full sandwich assay necessitates coating a solid phase support such as polystyrene or other surface capable of binding either covalently or non-covalently the polyclonal antibody. The antibody then captures and concentrates the antigen on the surface. Subsequent addition of APS reductase antibody conjugated to a color generating enzyme, such as horseradish peroxidase or alkaline phosphatase, results in the formation of a full sandwich comprising the primary bound antibody, antigen reacted with it and secondary antibody-enzyme conjugate attached to the reacted antigen.

Purified anti APS reductase antibody was prepared from immune rabbit serum by batch treatment with APS reductase-sepharose gel as described in "Laboratory Techniques in Biochemistry and Molecular Biology: Practice and Theory of Immunoassays" P. Tijssen, pages 110-114 (see earlier reference). Generally, pure APS reductase (20 mg) was incubated overnight with cyanogen bromide activated sepharose (700 mg). The resulting APS reductase-sepharose conjugate was washed repeatedly with 0.5M phosphate buffer pH 7.4 in 0.1M sodium chloride. The resulting APS reductase-sepharose conjugate was added to a 100 ml aliquot of pooled immune serum which had been previously diluted with an equal volume of buffer (0.5M phosphate, 0.1M sodium chloride) and the mixture was incubated overnight at 4° C. with constant stirring. The resulting APS reductase-sepharose-antibody conjugate was washed four times with the buffer (0.5M phosphate, 0.1M sodium chloride). The antibodies in the conjugate were eluted by lowering the pH to 2.1, collecting the supernatant fluid and rapidly readjusting its pH to pH 7.0 by adding 0.5M phosphate buffer. The affinity-purified antibody was then concentrated by precipitating it by adding ammonium sulfate to a concentration 50% of saturation. The recovered antibody (20 mg) was redissolved in 6 mL of solution containing 5 mM phosphate, 30 mM sodium chloride, 30 mM sodium azide.

Antibody (anti-APS reductase) was conjugated with peroxidase enzyme as described in "Laboratory Techniques in Biochemistry and Molecular Biology: Practice and Theory of Immunoassays" P. Tijssen, pages 236-240 (see earlier reference). Generally, peroxidase (5 mg) (Sigma Chemical CO.) was added to 1 mL of a solution of 0.1M sodium bicarbonate and 10 mM sodium periodate and incubated overnight at room temperature. The activated peroxidase (1 mL) was combined with 7 mg of APS reductase antibody contained in 1 mL of 0.1 sodium carbonate pH 9.2 for a total volume of 2 mL. The resulting solution was incubated for 3 hr. at 25° C. An equal volume (2 mL) of saturated ammonium sulfate was added which selectively precipitated the IgG molecules. The resulting precipitate, which consists of a mixture of free IgG and IgG-peroxidase conjugate was resuspended in 10 mL of a solution of 0.1M sodium phosphate, 0.1 sodium chloride and applied to a Con A sepharose gel (Sigma Chemical Co.) The IgG-peroxidase conjugate selectively bound to Con A and it was eluted from the Con A sepharose gel by the addition of excess of alpha-methyl D-mannopyranoside (100 mM) solution in PBS buffer at a pH of 7.2 and collected in a total volume of 3 mL.

To assay for APS reductase, anti-APS reductase (4 ug) was added to each of a number of wells of a microtiter plate. The plates containing the anti-APS reductase were incubated for 2 hr at 4° C. then washed four times with PBS containing TWEEN and gelatin. Different concentrations of APS reductase, (ranging from 320 to 4 ng) were added to separate wells. The plates were incubated for 2 hr at 25° C. The wells were washed four times with PBS buffer containing TWEEN and gelatin. Wells to which each concentration of APS reductase had been added then received each of three dilutions (1/1000, 1/5000, and 1/10,000) of anti-APS reductase-peroxidase conjugate. The plates with conjugate were incubated an additional 2 hr at 25° C. After further washing with PBS buffer containing TWEEN and gelatin to remove any unattached material, indicator substrate was added to each well and the concentration of the resulting color at O.D.$_{410}$ was determined. The results are shown in Table 6.

TABLE 6

| APS reductase | O.D.$_{410}$ | | |
|---|---|---|---|
| per well (ng) | 1/1000* | 1/5000* | 1/10,000* |
| 320 | 1.2 | 0.5 | 0.3 |
| 64 | 0.9 | 0.4 | 0.2 |
| 32 | 0.5 | 0.3 | 0.2 |
| 16 | 0.3 | 0.1 | 0.1 |
| 8 | 0.1 | 0.1 | 0.0 |
| 4 | 0.0 | 0.0 | 0.0 |

*Dilution of anti-APS reductase-peroxidase conjugate.

The results shown in Table 6 show that the antibodies in the immune serum made in response to the purified APS reductase from D. desulfuricans strain G100A can detect APS reductase in a full sandwich immunoassay.

While the detection of APS reductase by the antibodies in the immune serum made in response to the purified APS reductase from D. desulfuricans strain G100A has been demonstrated in two types of immune assays, it is presently believed that any assay capable of measuring the reaction product of APS reductase and its antibodies can be used.

We claim:

1. In a method for controlling sulfate-reducing bacteria in an aqueous environment, which method comprises collecting a sample of the environment, detecting the presence of any sulfate-reducing bacteria in the sample, and responsive to the presence of sulfate-reducing bacteria, treating the environment with an effective amount of bacteriocidal or bacteriostatic agents to kill or inhibit the growth of sulfate-reducing bacteria in the environment, the improvement comprising: detecting the presence of any sulfate-reducing bacteria in the sample by
  (a) preparing a lysate of said sample to release into said lysate adenosine 5'-phosphosulfate reductase (APS reductase) contained in said sulfate-reducing bacteria,
  (b) contacting at least a portion of the lysate with a first antibody specific for the APS reductase to form a first complex, and
  (c) detecting the first complex as an indication of the presence of sulfate-reducing bacteria.

2. The method of claim 1 wherein the first antibody is linked to a solid phase support and wherein step (b) further comprises either (1) contacting the first complex with a conjugate comprising (i) a second antibody specific for APS reductase and (ii) a color formation agent to form a second complex comprising the first complex and the conjugate or (2) contacting the portion of the lysate with the conjugate concurrently with or prior to the first antibody to form the second complex, and wherein step (c) comprises removing uncomplexed conjugate and adding a color development reagent to the second complex, whereby the color formation agent and color development reagent react to produce a colored product indicative of the presence of sulfate-reducing bacteria.

3. The method of claim 2 wherein the aqueous environment in which the sulfate-reducing bacteria are controlled is in a bore hole traversing a hydrocarbon containing subterranean formation or in the formation itself.

4. The method of claim 2 wherein the color formation agent is horseradish peroxidase or alkaline phosphatase and wherein the solid phase support comprises polystyrene onto which has been surface grafted glycidyl methacrylate having a plurality of antibody linking sites.

5. A method for detecting the presence of sulfate-reducing bacteria in a sample comprising:
  (a) preparing a lysate of said sample to release into said lysate adenosine 5'-phosphosulfate reductase (APS reductase) contained in said sulfate-reducing bacteria,
  (b) contacting at least a portion of the lysate with a first antibody specific for the APS reductase to form a first complex, and
  (c) detecting the first complex as an indication of the presence of sulfate-reducing bacteria.

6. The method of claim 5 wherein the first antibody is linked to a solid phase support and wherein step (b) further comprises either (1) contacting the first complex with a conjugate comprising (i) a second antibody specific for APS reductase and (ii) a color formation agent to form a second complex comprising the first complex and the conjugate or (2) contacting the portion of the lysate with the conjugate concurrently with or prior to the first antibody to form the second complex, and wherein step (c) comprises removing uncomplexed conjugate and adding a color development reagent to the second complex, whereby the color formation agent and color development reagent react to produce a colored product indicative of the presence of sulfate-reducing bacteria.

7. The method of claim 6 wherein the solid phase support comprises a surface graft polymer formed on an organic polymeric backbone.

8. The method of claim 7 wherein the color formation agent is horseradish peroxidase or alkaline phosphatase and wherein the solid phase support comprises polystyrene onto which has been surface grafted glycidyl methacrylate having a plurality of antibody linking sites.

* * * * *